US011205506B2

(12) United States Patent
Alkalay et al.

(10) Patent No.: US 11,205,506 B2
(45) Date of Patent: Dec. 21, 2021

(54) VERIFYING NATURAL LANGUAGE PROCESSING IN HEALTH CARE

(71) Applicant: International Business Machines Corporation, Armonk, NY (US)

(72) Inventors: Yael Alkalay, Brookline, MA (US); Jane Depgen, Boston, MA (US); Vincent Snagg, Cambridge, MA (US)

(73) Assignee: International Business Machines Corporation, Armonk, NY (US)

( * ) Notice: Subject to any disclaimer, the term of this patent is extended or adjusted under 35 U.S.C. 154(b) by 337 days.

(21) Appl. No.: 16/419,096

(22) Filed: May 22, 2019

(65) Prior Publication Data
US 2020/0372981 A1 Nov. 26, 2020

(51) Int. Cl.
| | |
|---|---|
| *G16H 10/60* | (2018.01) |
| *G16H 10/20* | (2018.01) |
| *A61B 5/00* | (2006.01) |
| *G16H 50/20* | (2018.01) |
| *G06F 40/20* | (2020.01) |
| *G06F 40/40* | (2020.01) |
| *G16H 15/00* | (2018.01) |
| *G16H 40/20* | (2018.01) |

(52) U.S. Cl.
CPC .......... *G16H 10/60* (2018.01); *A61B 5/4842* (2013.01); *G06F 40/20* (2020.01); *G06F 40/40* (2020.01);
(Continued)

(58) Field of Classification Search
CPC ........ G16H 10/60; G16H 10/20; G16H 50/20; G16H 15/00; G16H 40/20; G16H 40/67;
(Continued)

(56) References Cited

U.S. PATENT DOCUMENTS

| | | |
|---|---|---|
| 7,197,497 B2 | 3/2007 | Cossock |
| 8,862,614 B2 | 10/2014 | Pradhan et al. |

(Continued)

FOREIGN PATENT DOCUMENTS

| | | | |
|---|---|---|---|
| CN | 102194059 A | | 9/2011 |
| CN | 103793611 A | | 5/2014 |
| CN | 104665787 B | * | 8/2017 |

OTHER PUBLICATIONS

Grap, Mary Jo; Strickland, Dale; Tormey, Laura; Keane, Kim; Lubin, Shannon; et al. "Collaborative practice: development, implementation and evaluation of a weaning protocol for patients receiving mechanical ventilation." American Journal of Critical Care12.5: 454(7). Sep. (2003) (Year: 2003).*

(Continued)

*Primary Examiner* — Linh Giang Le
(74) *Attorney, Agent, or Firm* — Ryan Lewis; Edell, Shapiro & Finnan, LLC (57) ABSTRACT

A computer system visualizes medical information for a patient. Natural language processing techniques are applied to identify medical concepts within unstructured text of medical information. Values for the identified medical concepts are derived from combinations of values within the medical information. A visualization is generated for a selected derived value, wherein the visualization includes a plurality of interconnected nodes each associated with a corresponding information source utilized for determining the selected derived value, and wherein paths of the interconnected nodes in the visualization indicate the corresponding information sources utilized to produce the selected derived value. Information of a selected node of the visualization is updated based on user verification of the information of the selected node. The visualization is modified based on the updated information. Embodiments of the present invention further include a method and program product for visualizing medical information for a patient in substantially the same manner described above.

20 Claims, 8 Drawing Sheets

(52) U.S. Cl.
CPC .............. *G16H 10/20* (2018.01); *G16H 50/20* (2018.01); *G16H 15/00* (2018.01); *G16H 40/20* (2018.01)

(58) Field of Classification Search
CPC ........ G06F 40/20; G06F 40/40; G06F 40/169; G06F 40/30; A61B 5/4842; A61B 5/7435; A61B 5/7475; A61B 5/0022
See application file for complete search history.

(56) References Cited

U.S. PATENT DOCUMENTS

| | | | |
|---|---|---|---|
| 2002/0116300 A1* | 8/2002 | DeBusk | G06Q 10/06 705/29 |
| 2007/0016453 A1* | 1/2007 | Hiyama | G16H 15/00 705/3 |
| 2013/0035956 A1 | 2/2013 | Carmeli et al. | |
| 2014/0337355 A1 | 11/2014 | Heinze | |
| 2016/0196407 A1 | 7/2016 | Caballero et al. | |
| 2016/0070706 A1 | 10/2016 | Lee et al. | |
| 2020/0035359 A1* | 1/2020 | Erpenbach | G16H 50/70 |
| 2020/0176113 A1* | 6/2020 | Megerian | G06N 5/022 |

OTHER PUBLICATIONS

International Search Report and Written Opinion in corresponding International Application No. PCT/IB2020/064718, dated Aug. 31, 2020, 9 pages.

* cited by examiner

VERIFYING NATURAL LANGUAGE PROCESSING IN HEALTH CARE

BACKGROUND

1. Technical Field

Present invention embodiments relate to natural language processing, and more specifically, to verifying natural language processing in health care.

2. Discussion of the Related Art

A health-related attribute may refer to a characteristic of a person (e.g., age, employment status, history of tobacco usage, etc.), a medical attribute (e.g., H1C levels, cholesterol levels, etc.), and/or a medical concept (e.g., a medical diagnosis, a medical intervention code, a diabetes risk level, etc.). Artificial intelligence systems are increasingly employed by health care providers in order to improve clinical workflows, to accelerate the access to and discovery of patient health information, and to improve care quality. However, health professionals may struggle to trust the health-related information that is discovered and presented by artificial intelligence systems due to a lack of transparency or comprehension of how artificial intelligence systems generate information.

SUMMARY

According to one embodiment of the present invention, a computer system visualizes medical information for a patient. Natural language processing techniques are applied to identify medical concepts within unstructured text of medical information. Values for the identified medical concepts are derived from combinations of values within the medical information. A visualization is generated for a selected derived value, wherein the visualization includes a plurality of interconnected nodes each associated with a corresponding information source utilized for determining the selected derived value, and wherein paths of the interconnected nodes in the visualization indicate the corresponding information sources utilized to produce the selected derived value. Information of a selected node of the visualization is updated based on verification of the information of the selected node. The visualization is modified based on the updated information. Embodiments of the present invention further include a method and program product for visualizing medical information for a patient in substantially the same manner described above.

BRIEF DESCRIPTION OF THE DRAWINGS

Generally, like reference numerals in the various figures are utilized to designate like components.

DETAILED DESCRIPTION

Present invention embodiments relate to natural language processing, and more specifically, to verifying natural language processing in health care. A computing system may verify medical conclusions for patients by analyzing electronic health records of the patients along with other information, such as medical literature. For example, patient data may be processed using various natural language processing techniques to identify medical conditions of a patient. A medical conclusion may be generated by analyzing both structured and unstructured data. Structured data, for example, may include data that is organized, such as values in a medical form or a standard template, and unstructured data may include any data found in free-form text, such as a clinical note describing a patient.

In some cases, attributes of a medical conclusion may be derived from other attributes, forming a chain of structured and/or unstructured evidence for the derived attribute. At any point in the chain, an incorrect attribute may introduce a cascade of errors, leading to a faulty conclusion. Medical practitioners may therefore be reluctant to rely upon machine-generated medical conclusions when the conclusions cannot be verified. Present invention embodiments generate a visualization in which the evidence behind each inference may be observed, enabling medical conclusions to be verified and corrected when necessary. In particular, present invention embodiments may visualize a medical conclusion by presenting attributes, which are characteristics of a patient's health, and values for each attribute that describe the patient's status for the particular attribute. For example, an attribute may be "cancer stage," and the attribute may have a value of "2A." Attribute-value pairs may be visualized as nodes, which can be connected by links to indicate the relation of a node to another. Thus, a hierarchy of nodes may be generated to indicate the evidences upon which a particular conclusion is based.

Present invention embodiments enable verification of medical conclusions by presenting the structured and/or unstructured data sources upon which each attribute and value are based. Further, the machine learning model that is used to generate the conclusions may be updated in response to verification and/or correction of conclusions, thereby improving the accuracy of the model over time. Thus, medical conclusions may be generated in a manner that is efficient and more accurate than existing approaches, while also reducing costs and gaining the trust of medical practitioners.

It should be noted that references throughout this specification to features, advantages, or similar language herein do not imply that all of the features and advantages that may be realized with the embodiments disclosed herein should be, or are in, any single embodiment of the invention. Rather, language referring to the features and advantages is understood to mean that a specific feature, advantage, or characteristic described in connection with an embodiment is included in at least one embodiment of the present invention. Thus, discussion of the features, advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages will become more fully apparent from the following drawings, description and appended claims, or may be learned by the practice of embodiments of the invention as set forth hereinafter.

Figure 1:
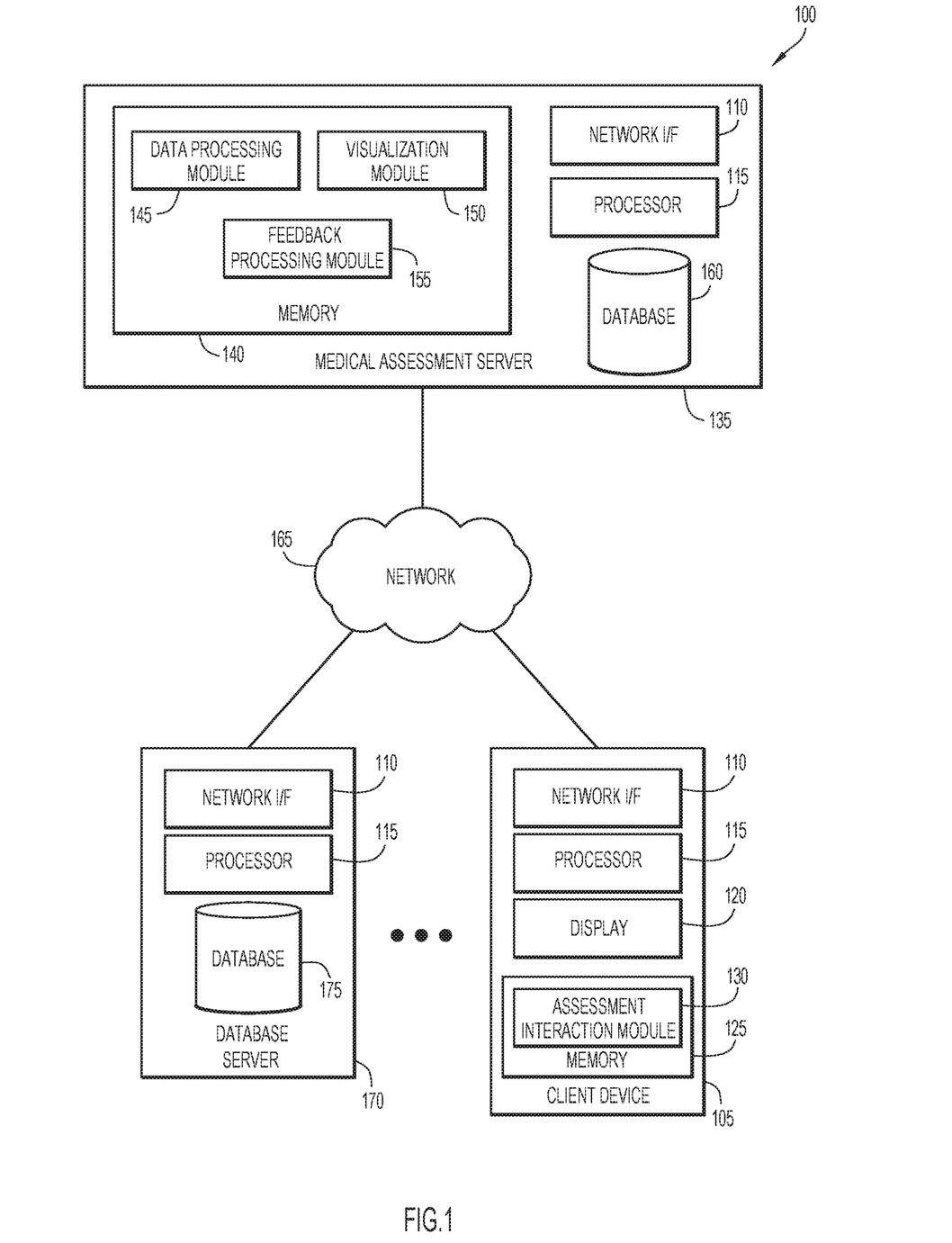
FIG. 1 is a block diagram depicting a computing environment for verifying medical conclusion in accordance with an embodiment of the present invention.

Present invention embodiments will now be described in detail with reference to the Figures. FIG. 1 is a block diagram depicting a computing environment 100 for generating medical conclusions in accordance with an embodiment of the present invention. As depicted, computing environment 100 includes a client device 105, a medical assessment server 135, and a database server 170. It is to be understood that the functional division among components of computing environment 100 have been chosen for purposes of explaining present invention embodiments and is not to be construed as a limiting example.

Client device 105 includes a network interface 110, at least one processor 115, a display 120, and memory 125. Memory 125 includes assessment interaction module 130. Client device 105 may include a laptop computer, a tablet computer, a netbook computer, a personal computer (PC), a desktop computer, a personal digital assistant (PDA), a smart phone, a thin client, or any programmable electronic device capable of executing computer readable program instructions. Network interface 110 enables components of client device 105 to send and receive data over a network, such as network 165. Client device 105 may include internal and external hardware components, as depicted and described in further detail with respect to FIG. 5.

Display 120 may include any electronic device capable of presenting information in a visual form. For example, display 120 may be a liquid crystal display (LCD), a cathode ray tube (CRT) display, a light-emitting diode (LED) display, an electronic ink display, and the like. Information relating to medical conclusions, such as attributes, values, and supporting evidences for attributes or values, may be presented to a user of client device 105 via display 120.

Assessment interaction module 130 may include one or more modules or units to perform various functions of present invention embodiments described below. Assessment interaction module 130 may be implemented by any combination of any quantity of software and/or hardware modules or units, and may reside within memory 125 of client device 105 for execution by a processor, such as processor 115.

Assessment interaction module 130 may enable a user of client device 105 to view and interact with information relating to medical conclusions of patients. Assessment interaction module 130 may present visualizations of medical conclusions to a user of client device 105, and may enable a user to manipulate the visualization to browse medical conclusions, verify medical conclusions, and/or update medical conclusions. Assessment interaction module 130 may receive data relating to medical conclusions from medical conclusion server 135 and its modules. A visualization of a medical conclusion may include a hierarchy of nodes that each include a particular attribute and a value for the attribute. For example, a node may have an attribute of "low density lipoprotein (LDL) level," and a value of "105 mg/dL." Nodes may also be linked to each other to form a hierarchy to indicate how attributes and values of some nodes are used as evidence to support attributes and values of other nodes. For example, a node with an attribute of "heart disease" and a value of "coronary artery disease" may be supported, at least in part, by another node with an attribute of "low density lipoprotein (LDL) level" and a value of "105 mg/dL."

A user may interact with a visualization of a patient's medical conclusion in order to verify and modify attributes and values. When a user selects a node, assessment interaction module 130 may present the evidence(s) from which the attribute and value of the node was derived. The user may provide input via assessment interaction module 130 to indicate that the user has verified an attribute and value. If a user disagrees with an attribute or value of a selected node, the user may update the node by providing input to update the attribute and/or value field. For example, if a node has an attribute of "prior surgery" and a value of "yes," and a user reviews a clinical note that was used to inform the value and concludes that the patient did not actually have a prior surgery, then the user may update the value to "no." Assessment interaction module 130 may transmit user feedback to medical conclusion server 135 in order to update a medical conclusion. Visualizations of health-related natural language processing may be depicted and described in further detail with respect to FIGS. 4A-4D.

Medical assessment server 135 includes a network interface 110, at least one processor 115, memory 140, and a database 160. Memory 140 includes a data processing module 145, a visualization module 150, and a feedback processing module 155. In various embodiments of the present invention, server 135 may include a laptop computer, a tablet computer, a netbook computer, a personal computer (PC), a desktop computer, a personal digital assistant (PDA), a smart phone, or any programmable electronic device capable of executing computer readable program instructions. Network interface 110 enables components of medical assessment server 135 to send and receive data over a network, such as network 165. Medical assessment server 135 may include internal and external hardware components, as depicted and described in further detail with respect to FIG. 5.

Data processing module 145, visualization module 150, and feedback processing module 155 may include one or more modules or units to perform various functions of present invention embodiments described below. Data processing module 145, visualization module 150, and feedback processing module 155 may be implemented by any combination of any quantity of software and/or hardware modules or units, and may reside within memory 140 of medical assessment server 135 for execution by a processor, such as processor 115.

Data processing module 145 may process structured and/or unstructured data to derive attributes and values for medical assessments. Data processing module 145 may employ known or other natural language processing techniques to process text found in structured and unstructured data. Structured data may include any patient data that has been organized, and unstructured data may include any free-form text, such as clinical notes, discharge summaries, or pathology reports. Data processing module 145 may use a machine learning model that updates in response to user feedback, thereby increasing the accuracy of natural language processing functions. In addition to medical concepts, data processing module 145 may also extract social concepts from patient data, which include any social or economic factors that can influence individual and group differences in health status. Data processing module 145 may produce annotations for medical and social concepts by identifying, categorizing, and coding the medical and social concepts that are extracted from patient data. In some embodiments, data processing module 145 analyzes patient data in view of other medical literature in order to derive attributes and values.

Visualization module 150 may generate visualizations of health-related natural language processing based on attributes and values extracted from patient data. Visualization module 150 may depict each attribute-value pair as a node, and may organize nodes into a hierarchical structure. Nodes may be connected by lines to indicate direct relationships, and may be organized into levels to denote a hierarchy. For example, nodes whose attribute-value pairs support a particular node's attribute and value may be placed at a level beneath the supported node. Visualization module 150 may label each node with the attribute and value of the node, and when a user selects a node, visualization module 150 may display the evidence that supports the attribute and value. For example, if the machine learning model of data processing module 145 derived a node's attribute and value from a particular clinical note, then visualization module 150 may display the text of the clinical note when a user selects the node. Visualization module 150 may enable an authorized device, such as client device 105, to access and interact with the data of a visualization. Data pertaining to each visualization, including attribute-value pairs and hierarchies of nodes, may be stored in database 160 of medical assessment server 135.

Feedback processing module 155 may receive and process user feedback that is provided when a user interacts with a visualization. User feedback may be received from assessment interaction module 130 of client device 105, and may include user verifications of attributes and values and corrections to attributes and values. When a user indicates that a particular node contains a correct attribute and value, feedback processing module 155 may instruct visualization module 150 to label the attribute and value as verified, and visualization module 150 may update the visualization accordingly. For example, a node whose attribute and value have been verified may be denoted as such by adding an icon to the node, changing a color of the node, or otherwise altering the appearance of the node. When a user corrects a node by providing an updated attribute or value, feedback processing module 155 may adjust the medical conclusion by updating the node and correcting any related derived attributes. When feedback processing module 155 adjusts a medical conclusion, visualization module 150 may update the visualization accordingly. In some embodiments, a node may contain multiple conflicting values, and a user can select a correct value that should be associated with the node's attribute.

Feedback processing module 155 may provide user feedback to data processing module 145 so that the machine learning model may be updated to improve the accuracy of the natural language processing function. In particular, aspects of the machine learning model that resulted in correctly-derived values may be strengthened, and aspects of the machine learning model that were incorrect may be modified to reduce the likelihood of identical or similar errors in the future. Thus, feedback processing module 155 enables generated medical conclusions to improve in accuracy over time.

Database 160 may include any non-volatile storage media known in the art. For example, database 160 can be implemented with a tape library, optical library, one or more independent hard disk drives, or multiple hard disk drives in a redundant array of independent disks (RAID). Similarly, data on database 160 may conform to any suitable storage architecture known in the art, such as a file, a relational database, an object-oriented database, and/or one or more tables. Database 160 may store data relating to generating and visualizing medical conclusions, including patient data, attributes and values, supporting evidence, visualization data, and medical literature.

Network 165 may include a local area network (LAN), a wide area network (WAN) such as the Internet, or a combination of the two, and includes wired, wireless, or fiber optic connections. In general, network 165 can be any combination of connections and protocols known in the art that will support communications between client device 105, medical assessment server 135, and/or database server 170 via their respective network interfaces 110 in accordance with embodiments of the present invention.

Database server 170 includes a network interface 110, at least one processor 115, and a database 175. In various embodiments of the present invention, database server 170 may include a laptop computer, a tablet computer, a netbook computer, a personal computer (PC), a desktop computer, a personal digital assistant (PDA), a smart phone, or any programmable electronic device capable of executing computer readable program instructions. Network interface 110 enables components of database server 170 to send and receive data over a network, such as network 165. Database server 170 may store structured and/or unstructured patient data. In some embodiments, database server 170 may be a server of a health care provider in which patient records are stored. Database server 170 may be accessible by medical assessment server 135 and/or client device 105 in order to generate and visualize medical conclusions based on patient data stored in database 175. Database server 170 may include internal and external hardware components, as depicted and described in further detail with respect to FIG. 5.

Database 175 may include any non-volatile storage media known in the art. For example, database 175 can be implemented with a tape library, optical library, one or more independent hard disk drives, or multiple hard disk drives in a redundant array of independent disks (RAID). Similarly, data on database 175 may conform to any suitable storage architecture known in the art, such as a file, a relational database, an object-oriented database, and/or one or more tables. Database 175 may store any patient data, including structured data and/or unstructured data. In some embodiments, medical assessment server 135 accesses database 175 periodically to retrieve updated patient data. Alternatively, medical assessment server 135 may access database 175 on an ad hoc basis when updated patient data becomes available.

Figure 2:
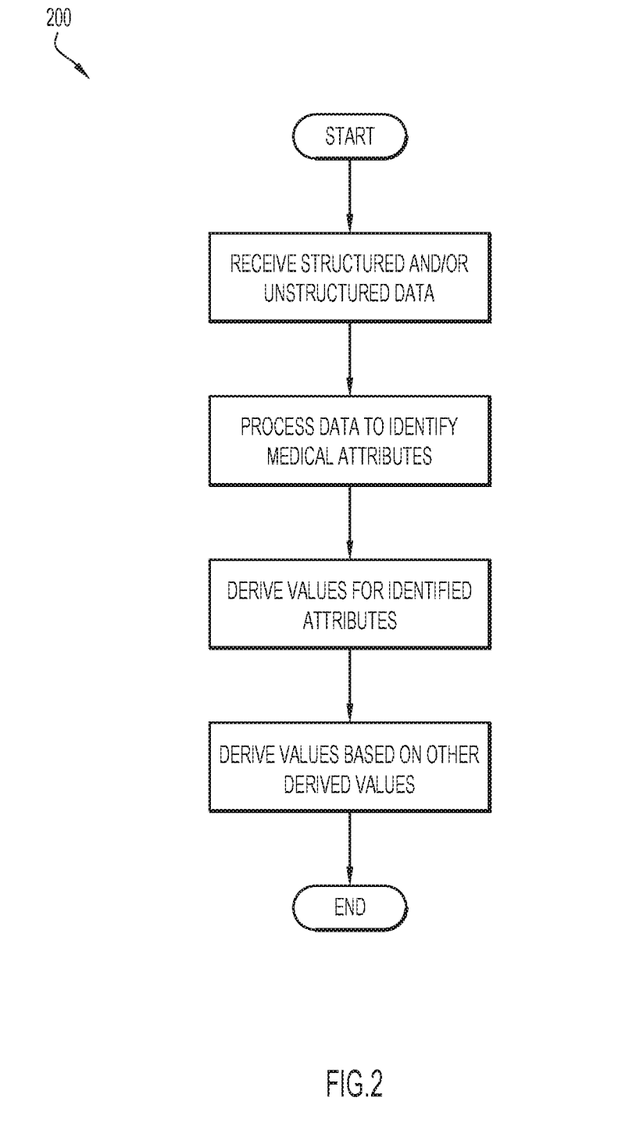
FIG. 2 is a flow chart depicting a method of processing patient data in accordance with an embodiment of the present invention.

FIG. 2 is a flow chart depicting a method 200 of processing patient data in accordance with an embodiment of the present invention.

Structured and/or unstructured data of a patient is received at operation 210. Patient data may include any data describing a patient's health and/or socioeconomic factors that may be relevant to a patient's health care. Patient data may be received from one or more sources, and may include electronic health records of a patient, clinical notes describing a patient, discharge summaries, laboratory reports, patient-provided information, and the like, including metadata. Patient data may be received by medical assessment server 135 from database server 170.

Patient data is processed to identify medical attributes at operation 220. Known or other natural language processing techniques may be employed to process structured and/or unstructured patient data in order to identify attributes of a patient. An attribute may include any medical or social concept that can be extracted from any source. Extraction of attributes may furthermore be based on the context of a data source. For example, patient data provided by a laboratory may be considered to be more accurate than patient data obtained by visual observation, and may therefore be weighted more heavily. Similarly, recent data sources may be prioritized over older data sources.

Values for the identified medical attributes are extracted at operation 230. Known or other natural language processing techniques may be employed to process structured and/or unstructured patient data in order to identify values for the identified medical attributes of a patient. Data processing module 145 may extract a value for each identified attribute. A value may be quantitative or qualitative, and an attribute may have multiple values or a range of values. Attributes and values may adhere to one or more ontologies or classification systems. In addition to extracting attributes and values, data processing module 145 may identify relations between two or more attributes-value pairs. For example, an attribute-value pair may be derived, at least in part, from another identified attribute and value.

Values are derived based on other derived values at operation 240. Known or other machine learning techniques may be employed in order to identify additional attribute-value pairs based on combinations of the information extracted at operation 230. For example, a patient's status with regard to a particular disease may be contingent on the patient having two or more symptoms, which may be identified in other attribute-value pairs.

Figure 3:
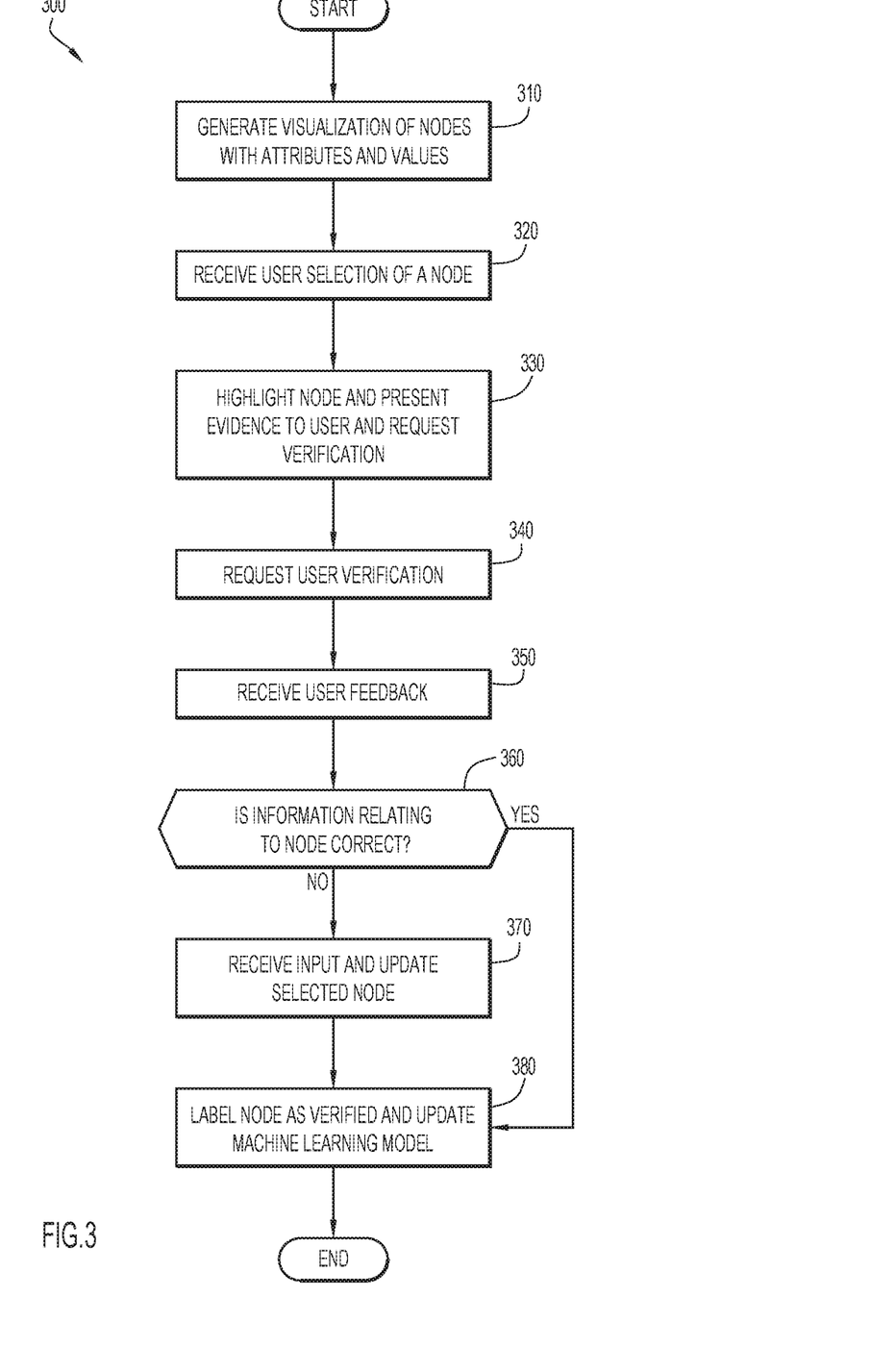
FIG. 3 is a flow chart depicting a method of generating a medical conclusion in accordance with an embodiment of the present invention.

FIG. 3 is a flow chart depicting a method 300 of generating a medical conclusion in accordance with an embodiment of the present invention.

A visualization of nodes with attributes and values is generated at operation 310. Visualization module 150 may generate a node for each attribute-value pair extracted by data processing module 145. Nodes may be organized into a hierarchical structure in which related nodes are linked to indicate their relationship. For example, a node's attribute and value may be informed by attributes and values of one or multiple other linked nodes. The visualization may comprise a graphical user interface that is presented to a user on display 120 of client device 105.

A user selection of a node is received at operation 320. A user may provide input to a graphical user interface of client device 105 to select a node. When a user selects a node, evidence for the node's attribute and value is presented to a user at operation 330, and verification is requested from the user at operation 340. Selection of a node may present the evidence, including annotations, upon which the node's attributes and values were based. Evidence may include any information sources that contain the patient data that was relied upon by data processing module 145 to extract the attribute and value of the selected node. When a user selects a node, assessment interaction module 130 may retrieve and present the evidence, such as a clinical note, that supports the node's attribute and value. In some embodiments, when a user selects a node, the node is highlighted or otherwise demarked, along with any other nodes whose attributes and values were relied upon, if any, to derive the attributes and values of the selected node. Assessment interaction module 130 may prompt a user submit feedback in order to verify the attribute and value presented. In particular, a user may indicate that the user agrees with the attribute and value, or the user may indicate disagreement by updating an attribute and/or value field for the node. If a node has two or more conflicting values, the user may select one of the values.

User feedback is received at operation 350. User feedback may include an indication that a node has been verified or an updated attribute or value for the node. User feedback may be received by feedback processing module 155 of medical assessment server 135 from client device 105.

Operation 360 determines whether the information of the node is correct. If a user's feedback comprises a verification, then the node is labeled as verified at operation 380. The node may receive a visual indication that it has been verified, such as a check-mark. If the information of the node is incorrect, the attribute or value of the node is updated based on the user's feedback at operation 370. When a node is corrected, the node may also be labeled as verified. Further, when a node is updated, related nodes may also be updated accordingly.

Additionally at operation 380, the machine learning model is updated based on the user's feedback. In particular, the machine learning model may be updated to reinforce correctly-determined conclusions (e.g., extracted attributes and values) and to avoid erroneous conclusions. The machine learning model can be r e-trained with datasets containing attributes and values that have been verified and/or updated based on user feedback.

Figure 4A:
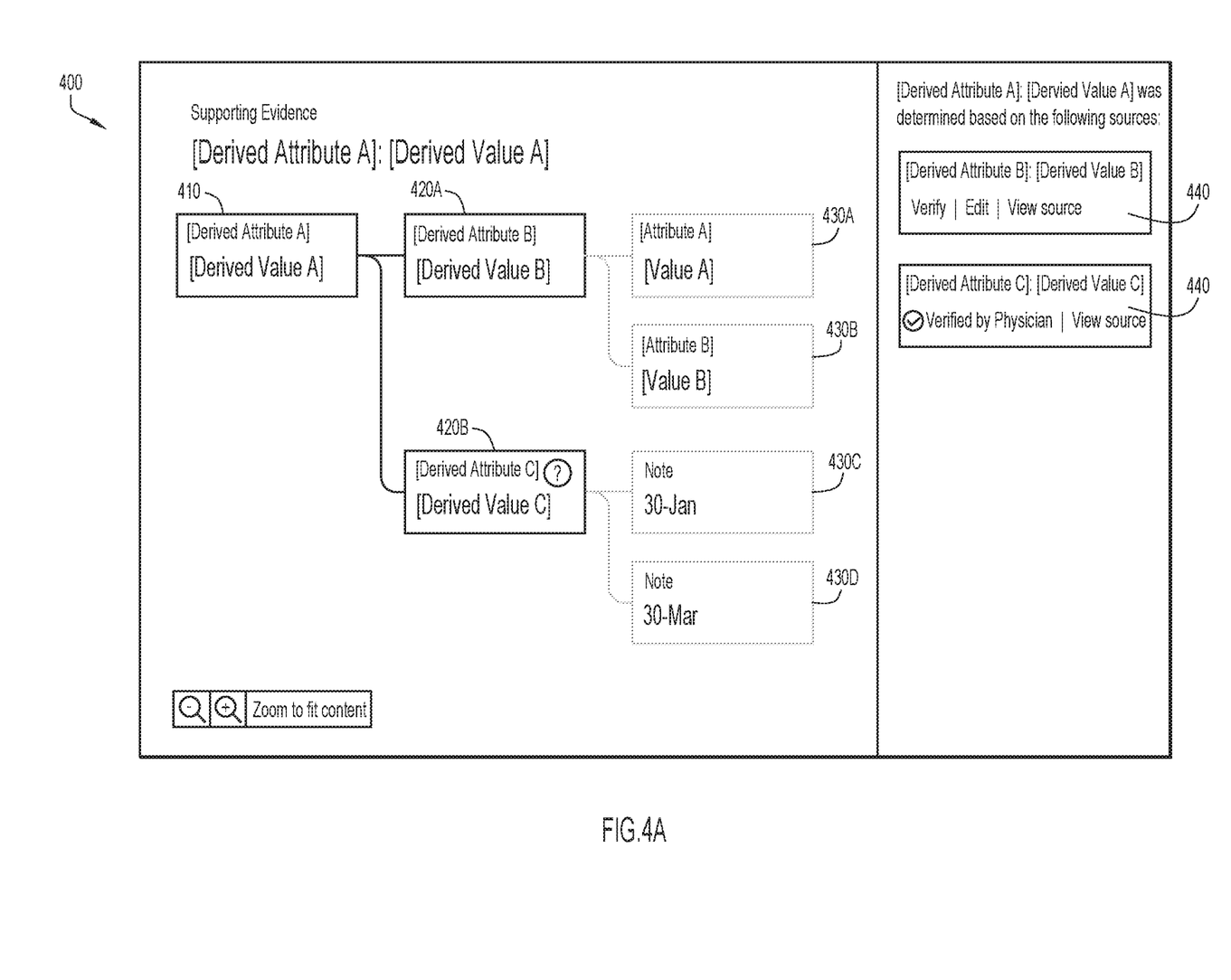
FIGS. 4A-4D are examples of a graphical user interface of an interactive visualization in accordance with an embodiment of the present invention.

FIGS. 4A-4D are examples of a graphical user interface 400 of an interactive visualization in accordance with an embodiment of the present invention. In FIG. 4A, node 410 has an attribute and a derived value. For example, an attribute may include "patient setting" and a value for that attribute may include "adjuvant." The attribute-value pair of node 410 is supported by nodes 420A and 420B, which are organized into a different level of the hierarchy. The attribute-value pair of node 420A is supported by the attributes and values of nodes 430A and 430B, and the attribute-value pair of node 420B is supported by two evidences, represented by nodes 430C and 430D. Thus, the attributes and values of some nodes, such as nodes 410, 420A, 430A and 430B, are supported by other derived attributes and values, while other nodes, such as node 420B, may be directly supported by evidence.

Figure 4B:
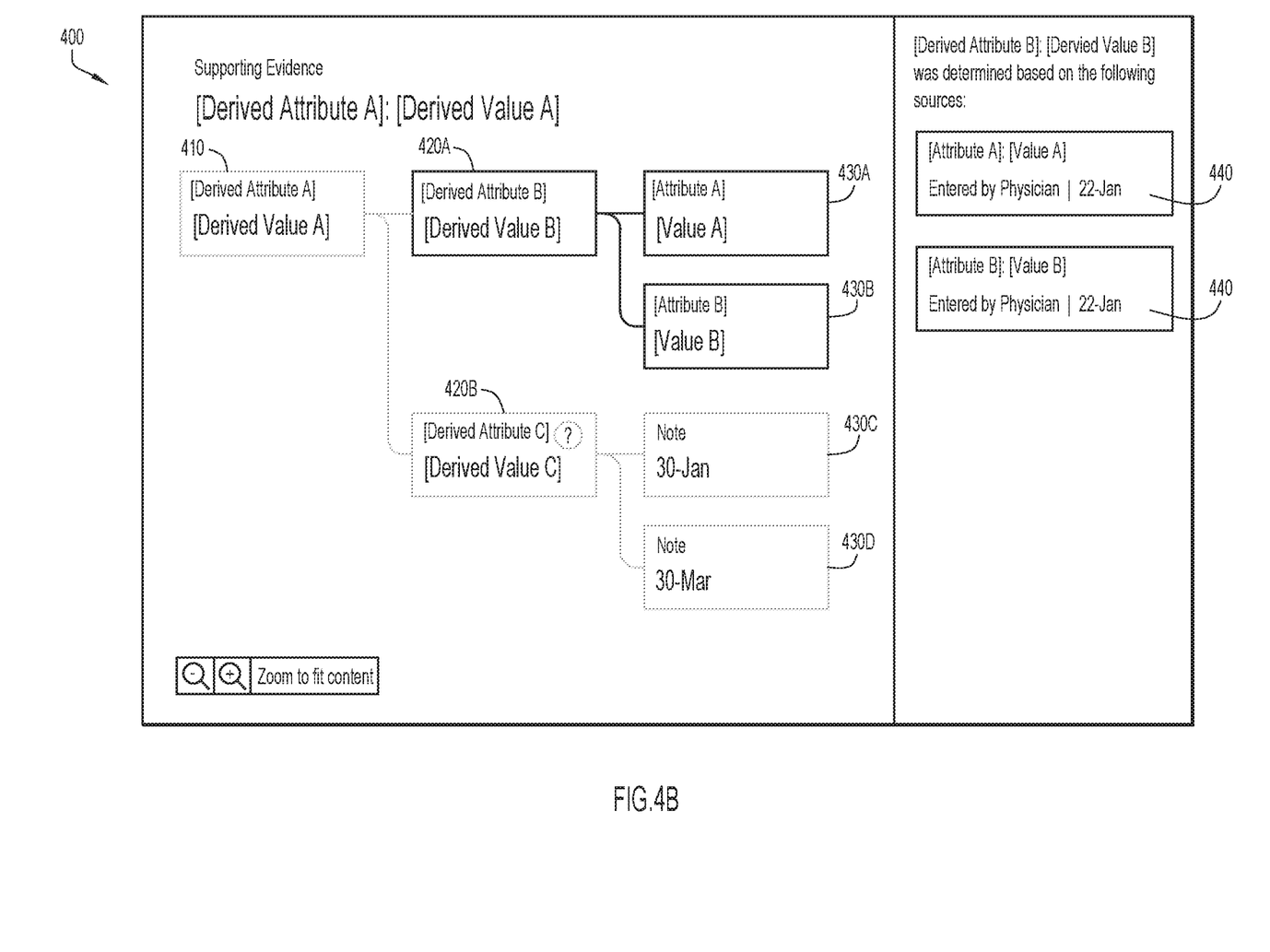
Figure 4C:
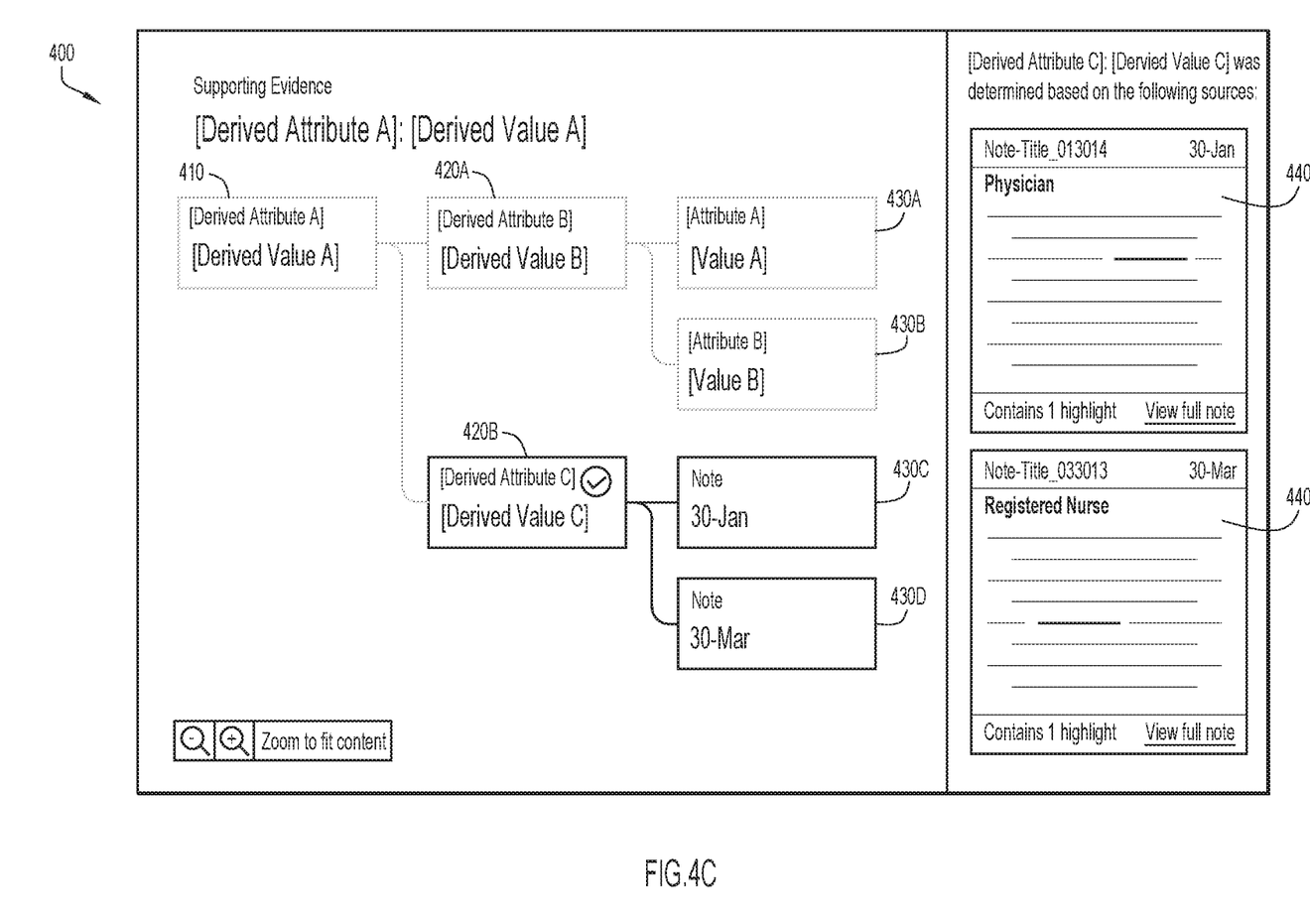

The evidence panel 440 depicts the evidence or evidences from which a node's attribute and value are derived. In FIG. 4A, the user has selected node 410, so evidence panel 440 shows that nodes 420A and 420B were used to support the finding of the derived attributes and values. In FIG. 4B, a user has selected node 420A, and evidence panel 440 is accordingly updated to show the sources for the attribute and value, which include nodes 430A and 430B. Likewise, FIG. 4C depicts an example in which node 420B has been selected, and evidence panel 440 includes summaries of the two evidences for the attribute and value of node 420B. In the depicted example, both evidence 430C and 430D are clinical notes, and the attribute and value of node 420B has thus been extracted by performing natural language processing on the free-form text of the clinical notes. FIG. 4C depicts an example in which a user has verified node 420B, which has been updated by changing the question mark to a check-mark. Alternatively, a user can provide an updated value for the attribute of 420B, such as by inputting a different value to replace the current value. In some embodiments, nodes may be labeled to distinguish nodes whose attributes and values have been derived using natural language processing on unstructured data sources from nodes whose attributes and values have been derived from structured data sources.

Figure 4D:
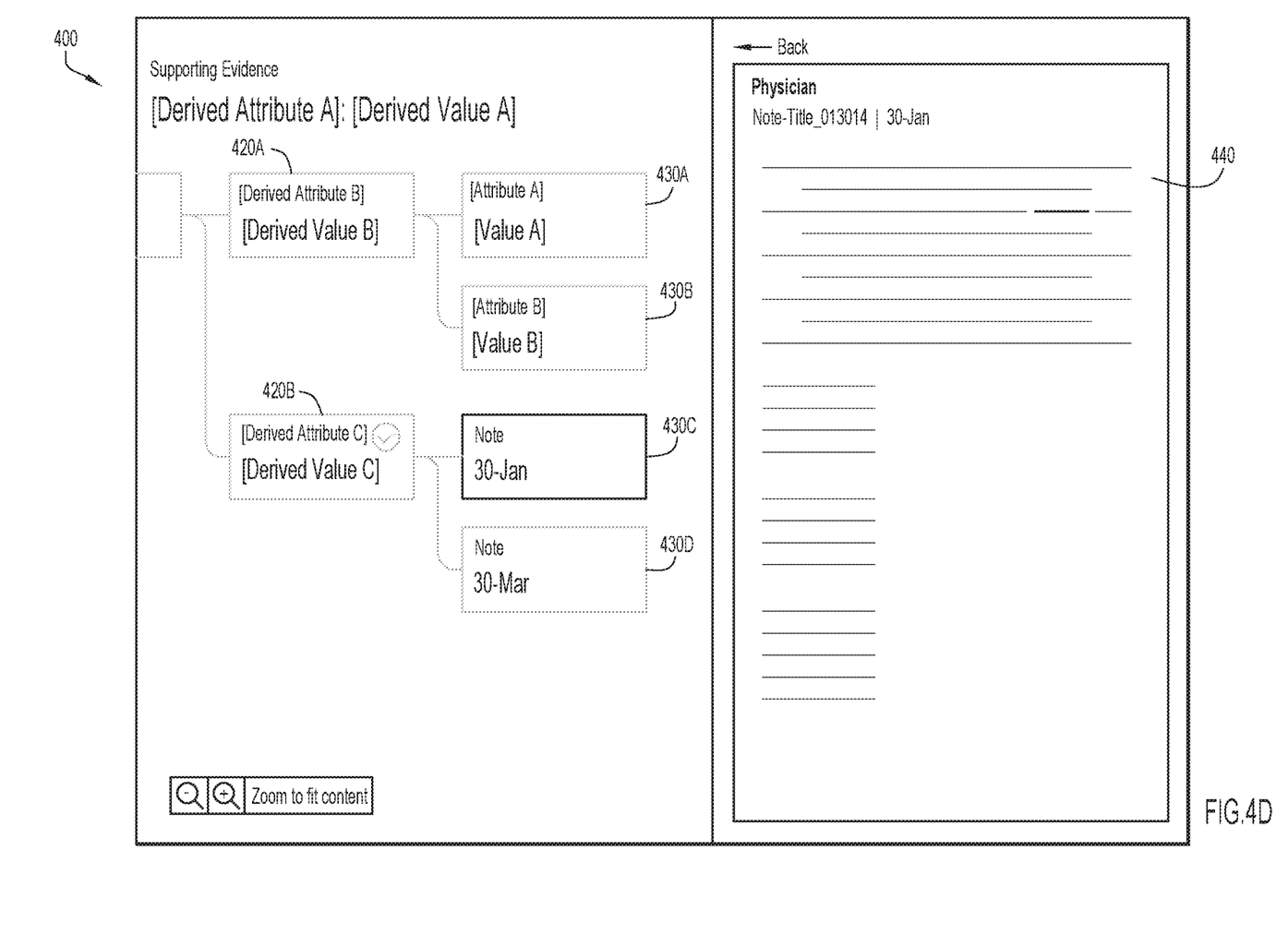

FIG. 4D depicts an example of graphical user interface 400 in which node 420C, a supporting evidence for node 420B, has been selected by a user. When a user selects an individual evidence, evidence panel 440 may be updated to present an expanded version of the evidence to the user. For example, the user may view the entire text of the clinical note dated January 30. Further, the portions of the unstructured data from which the attribute and value were derived may be highlighted or otherwise denoted for the user.

Figure 5:
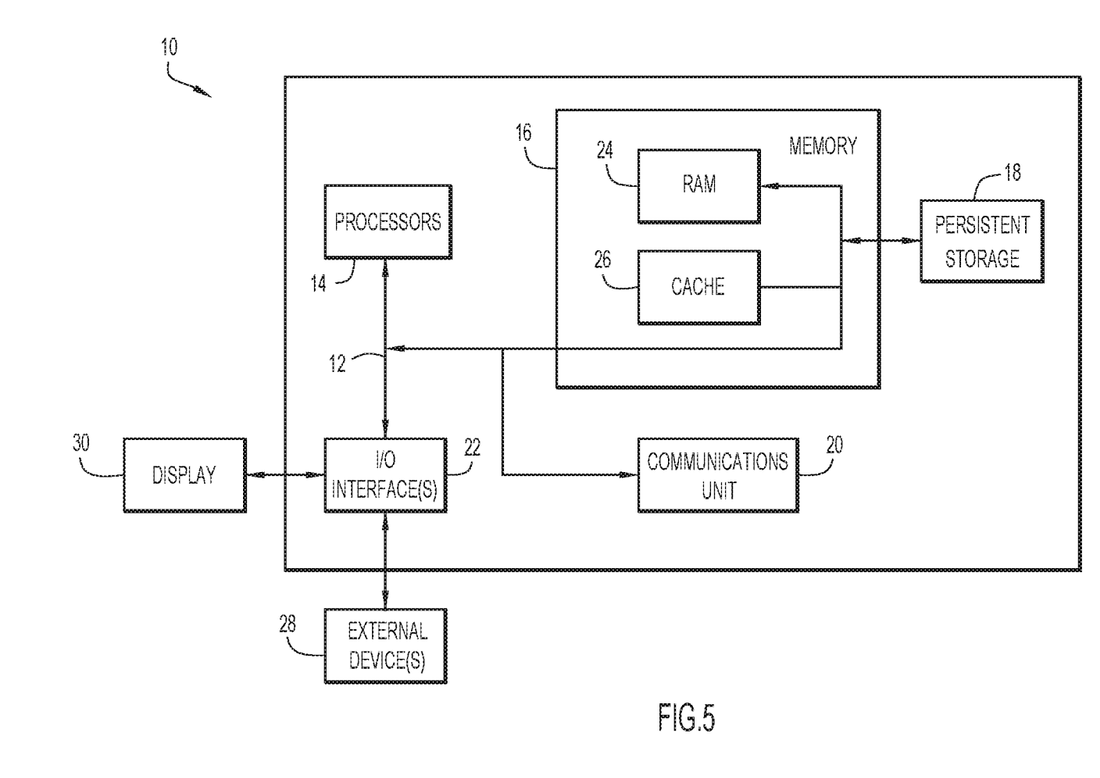
FIG. 5 is a block diagram depicting a computing device in accordance with an embodiment of the present invention.

FIG. 5 is a block diagram depicting components of a computer 10 suitable for executing the methods disclosed herein. Computer 10 may implement client device 105, medical assessment server 135, and/or database server 170 in accordance with embodiments of the present invention. It should be appreciated that FIG. 5 provides only an illustration of one embodiment and does not imply any limitations with regard to the environments in which different embodiments may be implemented. Many modifications to the depicted environment may be made.

As depicted, the computer 10 includes communications fabric 12, which provides communications between computer processor(s) 14, memory 16, persistent storage 18, communications unit 20, and input/output (I/O) interface(s) 22. Communications fabric 12 can be implemented with any architecture designed for passing data and/or control information between processors (such as microprocessors, communications and network processors, etc.), system memory, peripheral devices, and any other hardware components within a system. For example, communications fabric 12 can be implemented with one or more buses.

Memory 16 and persistent storage 18 are computer readable storage media. In the depicted embodiment, memory 16 includes random access memory (RAM) 24 and cache memory 26. In general, memory 16 can include any suitable volatile or non-volatile computer readable storage media.

One or more programs may be stored in persistent storage 18 for execution by one or more of the respective computer processors 14 via one or more memories of memory 16. The persistent storage 18 may be a magnetic hard disk drive, a solid state hard drive, a semiconductor storage device, read-only memory (ROM), erasable programmable read-only memory (EPROM), flash memory, or any other computer readable storage media that is capable of storing program instructions or digital information.

The media used by persistent storage 18 may also be removable. For example, a removable hard drive may be used for persistent storage 18. Other examples include optical and magnetic disks, thumb drives, and smart cards that are inserted into a drive for transfer onto another computer readable storage medium that is also part of persistent storage 18.

Communications unit 20, in these examples, provides for communications with other data processing systems or devices. In these examples, communications unit 20 includes one or more network interface cards. Communications unit 20 may provide communications through the use of either or both physical and wireless communications links.

I/O interface(s) 22 allows for input and output of data with other devices that may be connected to computer 10. For example, I/O interface 22 may provide a connection to external devices 28 such as a keyboard, keypad, a touch screen, and/or some other suitable input device. External devices 28 can also include portable computer readable storage media such as, for example, thumb drives, portable optical or magnetic disks, and memory cards.

Software and data used to practice embodiments of the present invention can be stored on such portable computer readable storage media and can be loaded onto persistent storage 18 via I/O interface(s) 22. I/O interface(s) 22 may also connect to a display 30. Display 30 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Data relating to verifying natural language processing in health care (e.g., patient data, derived attribute and value data, supporting evidences, visualization data, medical literature data, etc.) may be stored within any conventional or other data structures (e.g., files, arrays, lists, stacks, queues, records, etc.) and may be stored in any desired storage unit (e.g., database, data or other repositories, queue, etc.). The data transmitted between client device 105, medical assessment server 135, and/or database server 170 may include any desired format and arrangement, and may include any quantity of any types of fields of any size to store the data. The definition and data model for any datasets may indicate the overall structure in any desired fashion (e.g., computer-related languages, graphical representation, listing, etc.).

Data relating to verifying natural language processing in health care (e.g., patient data, derived attribute and value data, supporting evidences, visualization data, medical literature data, etc.) may include any information provided to, or generated by, client device 105, medical assessment server 135, and/or database server 170. Data relating to verifying natural language processing in health care may include any desired format and arrangement, and may include any quantity of any types of fields of any size to store any desired data. The data relating to verifying natural language processing in health care may include any data collected about entities by any collection mechanism, any combination of collected information, and any information derived from analyzing collected information.

The present invention embodiments may employ any number of any type of user interface (e.g., Graphical User Interface (GUI), command-line, prompt, etc.) for obtaining or providing information (e.g., data relating to verifying natural language processing in health care), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

It will be appreciated that the embodiments described above and illustrated in the drawings represent only a few of the many ways of verifying natural language processing in health care.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., server software, networking software, assessment interaction module 130, data processing module 145, visualization module 150, feedback processing module 155, etc.). These systems may include any types of monitors and input devices (e.g., keyboard, mouse, voice recognition, etc.) to enter and/or view information.

It is to be understood that the software (e.g., server software, networking software, assessment interaction module 130, data processing module 145, visualization module 150, feedback processing module 155, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., server software, networking software, assessment interaction module 130, data processing module 145, visualization module 150, feedback processing module 155, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., data relating to verifying natural language processing in health care). The database system may be implemented by any number of any conventional or other databases, data stores or storage structures (e.g., files, databases, data structures, data or other repositories, etc.) to store information (e.g., data relating to verifying natural language processing in health care). The database system may be included within or coupled to the server and/or client systems. The database systems and/or storage structures may be remote from or local to the computer or other processing systems, and may store any desired data (e.g., data relating to verifying natural language processing in health care).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create mechanisms for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method of visualizing medical information for a patient comprising:
 applying, via a processor, a trained natural language processing model to identify medical concepts within unstructured text of medical information;
 deriving, via the processor, values for the identified medical concepts from combinations of values within the medical information;
 generating, via the processor, a visualization for a selected derived value, wherein the visualization includes a plurality of interconnected nodes each associated with a corresponding information source utilized for determining the selected derived value, and wherein paths of the interconnected nodes in the visualization indicate the corresponding information sources utilized to produce the selected derived value;
 updating, via the processor, information of a selected node of the visualization based on verification of the information of the selected node, wherein the verification is based on user feedback, and wherein the trained natural language processing model is updated based on the updated information; and modifying the visualization, via the processor, based on the updated information.

2. The computer-implemented method of claim 1, wherein the trained natural language processing model further identifies social concepts, categorizes and codes the identified medical and social concepts, and produces annotations for the identified medical and social concepts.

3. The computer-implemented method of claim 1, wherein information of the selected node includes values and the annotations for the corresponding information source, and updating the information of the selected node further comprises:

updating one or more from a group of the annotations and values.

4. The computer-implemented method of claim 1, wherein the corresponding information source of the selected node includes notes of a medical provider, and the method further comprises:

presenting the notes of the medical provider associated with the selected node concurrently with the visualization.

5. The computer-implemented method of claim 1, further comprising:

highlighting the selected node and one or more nodes of the visualization associated with information sources utilized to produce a derived value for the selected node.

6. The computer-implemented method of claim 1, further comprising:

indicating in the visualization a verified status of the selected node in response to the verification of the information of the selected node.

7. The computer-implemented method of claim 1, wherein the plurality of interconnected nodes are arranged in a hierarchy, and wherein a derived value of a node in a path of the hierarchy is based on a corresponding source associated with each of one or more prior nodes in the path.

8. The computer-implemented method of claim 1, further comprising:

identifying, by a user, attributes in the visualization determined from application of the trained natural language processing model, wherein the identified attributes include structured and unstructured attributes; and verifying the identified attributes by the user and providing a verification status tag to nodes associated with the verified attributes.

9. A computer system for visualizing medical information for a patient, the computer system comprising:

one or more computer processors;
one or more computer readable storage media;
program instructions stored on the one or more computer readable storage media for execution by at least one of the one or more computer processors, the program instructions comprising instructions to:

apply a trained natural language processing model to identify medical concepts within unstructured text of medical information;

derive values for the identified medical concepts from combinations of values within the medical information;

generate a visualization for a selected derived value, wherein the visualization includes a plurality of interconnected nodes each associated with a corresponding information source utilized for determining the selected derived value, and wherein paths of the interconnected nodes in the visualization indicate the corresponding information sources utilized to produce the selected derived value;

update information of a selected node of the visualization based on verification of the information of the selected node, wherein the verification is based on user feedback, and wherein the trained natural language processing model is updated based on the updated information; and modify the visualization based on the updated information.

10. The computer system of claim 9, wherein the program instructions to apply the trained natural language processing model further comprise instructions to identify social and medical concepts, categorize and code the identified medical and social concepts, and produce annotations for the identified medical and social concepts.

11. The computer system of claim 9, wherein information of the selected node includes values and the annotations for the corresponding information source, and wherein the program instructions to update the information of the selected node further comprise instructions to:

update one or more from a group of the annotations and values.

12. The computer system of claim 9, wherein the corresponding information source of the selected node includes notes of a medical provider, and further comprising instructions to:

present the notes of the medical provider associated with the selected node concurrently with the visualization.

13. The computer system of claim 9, further comprising instructions to:

indicate in the visualization a verified status of the selected node in response to the verification of the information of the selected node.

14. The computer system of claim 9, wherein the plurality of interconnected nodes are arranged in a hierarchy, and wherein a derived value of a node in a path of the hierarchy is based on a corresponding source associated with each of one or more prior nodes in the path.

15. The computer system of claim 9, further comprising instructions to:

identify, by a user, attributes in the visualization determined from application of the trained natural language processing model, wherein the identified attributes include structured and unstructured attributes; and verify the identified attributes by the user and provide a verification status tag to nodes associated with the verified attributes.

16. A computer program product for visualizing medical information for a patient, the computer program product comprising one or more computer readable storage media collectively having program instructions embodied therewith, the program instructions executable by a computer to cause the computer to:

apply a trained natural language processing model to identify medical concepts within unstructured text of medical information;

derive values for the identified medical concepts from combinations of values within the medical information;

generate a visualization for a selected derived value, wherein the visualization includes a plurality of interconnected nodes each associated with a corresponding information source utilized for determining the selected derived value, and wherein paths of the interconnected nodes in the visualization indicate the corresponding information sources utilized to produce the selected derived value;

update information of a selected node of the visualization based on verification of the information of the selected node, wherein the verification is based on user feedback, and wherein the trained natural language processing model is updated based on the updated information; and modify the visualization based on the updated information.

17. The computer program product of claim 16, wherein the program instructions to apply the trained natural language processing model further comprise instructions to identify social concepts, categorize and code the identified medical and social concepts, and produce annotations for the identified medical and social concepts.

18. The computer program product of claim 16, wherein information of the selected node includes values and the annotations for the corresponding information source, and wherein the program instructions to update the information of the selected node further comprise instructions to:

update one or more from a group of the annotations and values.

19. The computer program product of claim 16, wherein the corresponding information source of the selected node includes notes of a medical provider, and further comprising instructions to:

present the notes of the medical provider associated with the selected node concurrently with the visualization.

20. The computer program product of claim 16, wherein the plurality of interconnected nodes are arranged in a hierarchy, and wherein a derived value of a node in a path of the hierarchy is based on a corresponding source associated with each of one or more prior nodes in the path.

* * * * *